United States Patent [19]

Laties et al.

[11] Patent Number: 5,385,939

[45] Date of Patent: Jan. 31, 1995

[54] GABA-ERGIC MODULATION OF EYE GROWTH

[75] Inventors: Alan M. Laties, Philadelphia; Richard A. Stone, Havertown, both of Pa.

[73] Assignee: The Trustees of the University of Pennsylvania, Philadelphia, Pa.

[21] Appl. No.: 56,056

[22] Filed: Apr. 30, 1993

[51] Int. Cl.$^6$ ................. A61K 31/195; A61K 31/205
[52] U.S. Cl. ..................... 514/561; 514/554; 514/912
[58] Field of Search ................. 514/561, 554, 912

[56] References Cited

U.S. PATENT DOCUMENTS

| | | | |
|---|---|---|---|
| 4,865,599 | 9/1989 | Chiou | 424/427 |
| 5,055,302 | 10/1991 | Laties et al. | 424/427 |
| 5,122,522 | 6/1992 | Laties et al. | 514/220 |

OTHER PUBLICATIONS

Mosinger et al., "GABA-like Immunoreactivity in the Vertebrate Retina: A Species Comparison", *Exp. Eye Res.* 42: 631–644 (1986).

Fiszer De Plazas et al., "Light and Dark Adaptation Influences GABA Receptor Sites in the Chick Retina", *Neurochemical Research*, 11: 973–981 (1986).

Ikeda, et al., "Actions of baclofen and phaclofen upon ON- and OFF-ganglion cells in the cat retina," *European J. of Pharm.* 190: 1 (1990).

*Primary Examiner*—Zohreh Fay
*Attorney, Agent, or Firm*—Woodcock Washburn Kurtz Mackiewicz & Norris

[57] ABSTRACT

A composition for the inhibition of the abnormal postnatal axial growth of the eye of a maturing animal which comprises a pharmaceutically effective amount of a gamma aminobutyric acid antagonist relatively selective for $GABA_B$ receptors in the cells of the eye, said antagonist present in a carrier or diluent suitable for ocular administration. A suitable antagonist is 2-OH saclofen.

4 Claims, 1 Drawing Sheet

GABA-ERGIC MODULATION OF EYE GROWTH

GOVERNMENT SUPPORT

This work was supported in part by research grants from the National Institutes of Health-National Eye Institute, grant numbers EY05454 and EY07354. The United States Government may have certain rights in this invention.

BACKGROUND OF THE INVENTION

This invention relates to control of ocular development and, more particularly, to the treatment of the eye to control the development of myopia (commonly known as nearsightedness).

It has been estimated that about one of every four persons on earth suffers from myopia. About one-half or more of these cases are axial myopia, i.e., an elongation of the eye along the visual axis.

At birth, the human eye is about two-thirds adult size and is even at that size relatively short in the axial direction. As a consequence, young children tend to be farsighted. During childhood, as the eye grows, there is a compensatory fine tuning of the optical properties of the cornea and lens to the increasing ocular length. Often the entire process is virtually perfect and no correction is needed for sharp vision at distance; the eye is emmetropic. When regulatory failure in this finely tuned process occurs, it usually goes toward a lengthened eye. As a result, distant images focus in front of the plane of the retina and axial myopia results. If, on the other hand, the regulatory failure leads to an eye whose ocular length is too short, near images focus behind the plane of the retina and the result is hyperopia (commonly known as farsightedness).

Over the years, many theories have been put forth to explain the development of myopia, e.g., inheritance, excessive near work, and environmental influences such as hours of sunshine, diet, etc. From these theories many preventative measures have been proposed including spectacles, eye exercise, eye rest, cycloplegia, and other drug therapies. The clinical literature on the subject is massive.

Based on a theory that substantial use of the eye by children for reading leads to the development of permanent nearsightedness or myopia, many remedies directed at the focussing mechanism at the front of the eye have been proposed. Largely these have been attempts either to block near focus through topical application of drugs or to remove any need for near focus through use of plus lenses that in effect perform the near focus task. Topical drugs that relax the focussing muscle of the eye, the ciliary muscle, are called cycloplegics and have been available for a century.

Some clinical studies have suggested that atropine, a long-acting cycloplegic, applied topically to the eye may retard development of myopia. Atropine treatment, however, is not practical: it causes dilation of the pupil, which results in light sensitivity, and its action to inhibit ocular focussing impairs near visual work like reading. In addition to the discomfort to the patient, there are indications that excess light can harm the retina and questions have been raised concerning the danger of the long-term use of atropine (or other strong cycloplegics) on the retina when exposed to bright light.

There is now substantial evidence to link the posterior part of the eye, specifically image quality at the retina and hence an extension of the nervous system, to the postnatal regulation of ocular growth. There is significant evidence of myopia resulting in an eye that is subjected to retinal image degradation. It has been shown that axial myopia can be experimentally induced, in either birds or primates, in an eye in which the retina is deprived of formed images, e.g., by suturing the eyelids or wearing an image-diffusing goggle. The experimental myopia induced in primates such as monkeys mimics the common axial myopia of humans.

Thus, the phenomenon of an animal's vision process apparently contributes to the feedback mechanism by which postnatal ocular growth is normally regulated and refractive error is determined. This indicates that this mechanism is neural and likely originates in the retina.

U.S. Pat. No. 5,055,302, to Laties and Stone, discloses a method of controlling the abnormal postnatal growth of the eye of a maturing animal using vasoactive intestinal peptide (VIP), PH1 or analogues of these peptides. These peptides were found to inhibit axial elongation of a myopic eye.

U.S. Pat. No. 5,122,522, to Laties and Stone, discloses a method of controlling the abnormal postnatal growth of the eye of a maturing animal using pirenzepine. Axial elongation of a myopic eye was inhibited upon application of pirenzepine.

Gamma aminobutyric acid, GABA, an amino acid present in the central nervous system, is also present in the eye. Mosinger et al., "GABA-like Immunoreactivity in the Vertebrate Retina: A Species Comparison", *Exp. Eye Res.* 42, 631–644 (1986). Gamma aminobutyric acid has two types of receptors: $GABA_A$ receptors and $GABA_B$ receptors. $GABA_A$ receptors preferentially bind the agonist muscimol and the antagonist bicuculline. $GABA_B$ receptors preferentially bind the agonist baclofen and the antagonist 2-OH saclofen. For purposes of this application, an agonist is an agent that activates a receptor, leading to an intracellular response. Thus, agonists mimic the effects of endogenous regulatory compounds. An antagonist, for the purposes of this discussion, is an agent that effectively inhibits the action of an agonist thereby inhibiting excessive or abnormal postnatal axial growth of the eye of a maturing animal. The antagonist is useful under conditions ordinarily leading to excessive or abnormal axial growth. GABA receptors are present in chick retina, see Fiszer De Plazas et al., "Light and Dark Adaptation Influences GABA Receptor Sites in the Chick Retina", *Neurochemical Research,* 11, 7, 973–981 (1986); as well as other vertebrate retinas.

SUMMARY OF THE INVENTION

The present invention provides methods and compositions for regulating the axial growth of an animal's eye. The methods of the invention comprise administration of an effective amount of 2-OH saclofen, a GABA receptor antagonist, active at the $GABA_B$ receptor. This invention is more particularly pointed out in the appended claims and is described in its preferred embodiments in the following description.

DETAILED DESCRIPTION OF THE INVENTION

Figure 1:
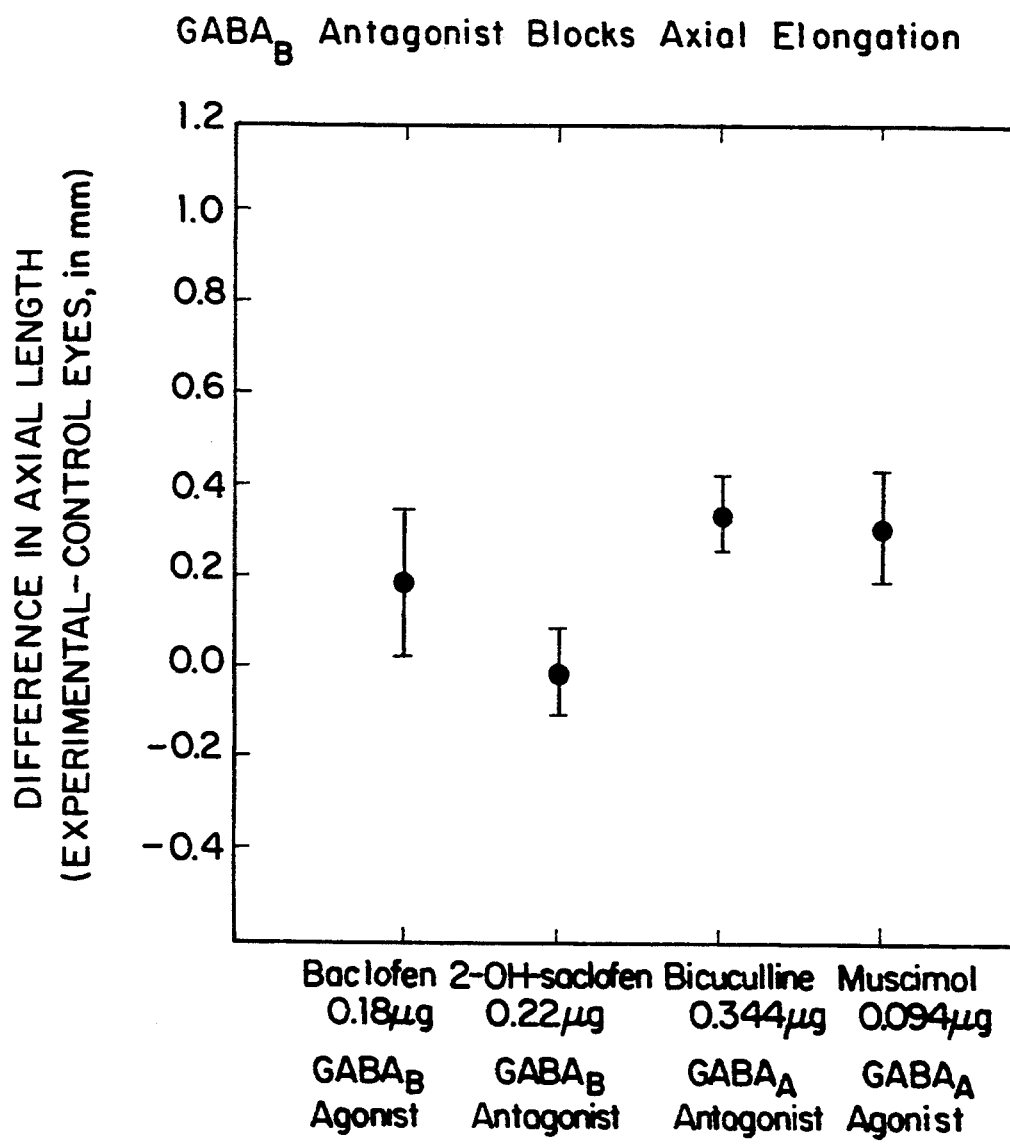
FIG. 1 shows the effect of 2-OH saclofen, a $GABA_B$ antagonist, in inhibiting axial growth of the eye. The failure of baclofen, bicuculline and muscimol in inhibiting axial growth is also evident.

In the ordinary visual function of the eye of an animal, light forming an image passes through the lens and is received by the retina, a neural tissue embryologically related to the brain. The retina transmits this information to the optic nerve which sends it on to the brain.

Retinal neurochemicals (i.e., neuro-active chemical compounds) are key ingredients in the vision process. Specifically, light forming the image is sensed by the light receptors, the rods and cones, of the retina. These photoreceptors act as transducers changing light energy into electrical and/or chemical signals.

In the regular process of transmitting the image information to the brain, retinal nerve cells, in association with the photoreceptors, release neurochemicals and pass electrical signals transmitting information to adjacent retinal cells as parts of a network in the retina leading to the formulation and qualities of the signals that later go to the brain via optic nerve.

In accordance with this invention, it has been found that a $GABA_B$ antagonist is effective in inhibiting the axial elongation myopia ordinarily produced by ocular image deprivation in the chick. A method of controlling the abnormal postnatal growth of the eye of a maturing animal which comprises the ocular administration of a therapeutically effective amount of a $GABA_B$ antagonist and a method of inhibiting the abnormal postnatal axial-growth of the eye of a maturing animal during conditions ordinarily leading to said abnormal growth, which comprises administering to said eye during postnatal maturation a therapeutically effective amount of 2-OH saclofen in a carrier or diluent buffered to a pH suitable for ocular administration are embodiments of the present invention.

Further, the present invention includes a composition for the inhibition of the abnormal postnatal axial growth of the eye of a maturing animal which comprises a pharmaceutically effective amount of a gama aminobutyric acid antagonist selective in inhibiting axial growth of the eye where the antagonist is present in a carrier or diluent buffered to a pH suitable for ocular administration.

A method of alleviating and controlling the development of amblyopia in the eye of a primate animal which comprises administering to such animal a therapeutically effective amount of a gamma aminobutyric acid antagonist relatively selective in inhibiting axial growth of the eye is also an embodiment of the present invention.

As stated herein, the gamma aminobutyric acid agent for use in this invention is relatively selective in inhibiting axial growth of the eye. Possible $GABA_B$ antagonists useful in the invention include, and are not limited to 2-OH saclofen, phaclofen, 5-aminovaleric acid, 3-aminopropyl (diethoxymethyl) phosphinic acid, 3-aminopropyl (n-hexyl) phosphinic acid, and 3-aminopropyl phosophonic acid. 2-OH saclofen is a representative preferred agent.

The affinity and relative affinity of gamma aminobutyric acid antagonists for $GABA_B$ receptors can be determined by means known in the art.

This invention is now described by the following example. This example is not to be construed as limiting the scope of the appended claims.

EXAMPLE

Form-deprivation myopia was induced in day-old White Leghorn chicks under aseptic conditions and ether anesthesia. One eyelid of the chicks was sutured which does not block vision. Translucent vision is permitted through the eyelid. The chicks were maintained on a 12 hour light:dark cycle. The sutured eyes were treated with either 2-OH saclofen (0.22 µg), baclofen (0.18 µg), bicuculline (0.344 µg), muscimol (0.094 µg) or saline solution as a control. The contralateral unsutured open eye served as a control. Sample populations were n=7, n=7, n=10, n=7 and n=32, respectively. All agents were injected daily subconjunctivally during the light cycle. At two weeks of age the animals were sacrificed and axial and equatorial dimensions of unfixed eyes were measured with vernier calipers independently by two observers. Lid-sutured chick eyes treated with baclofen, bicuculline, muscimol and saline solution developed axial elongation while those treated with 2-OH saclofen had a virtual blockade of axial elongation. TABLE I and FIG. 1 illustrate the effects of drug therapy on the growth of lid-sutured chick eyes. The average increase in axial length is the difference, deprived eye minus contralateral unsutured eye, for the number (n) of animals tested.

TABLE I

| Drug | Dose (µg) | Increased Axial length (mm) | n | p |
|---|---|---|---|---|
| 2-OH saclofen | 0.22 | −0.01 | 7 | <0.003 |
| baclofen | 0.18 | 0.18 | 7 | ns |
| bicuculline | 0.344 | 0.34 | 10 | ns |
| muscimol | 0.094 | 0.29 | 7 | ns |
| Saline solution | | 0.36 | 32 | ns | ns = not significant

Based on a one-way analysis of variance, there is significant effect on axial length, p<0.003 for 2-OH saclofen at 0.22 µg/day and no significant difference for the groups treated with baclofen, bicuculline and muscimol.

It is expected that known $GABA_B$ antagonists, including and not limited to phaclofen and 5-aminovaleric acid, can be used in the above example in place of 2-OH saclofen to obtain similar results in the inhibition of axial growth of the chick during maturation. As in the study of ganglion cell signalling by Ikeda, et al., *European J. of Pharm.* 1990, 190:1, 2-OH saclofen was chosen because of its high selectivity for $GABA_B$ receptors.

Treatment to inhibit axial-elongation myopia during maturation of an animal can be administered by the use of the agent in eye drops. Indeed, in the vast majority of cases, treatment agents are administered to human eyes by the application of eye drops. Eye drops are typically made up at a concentration of active agent between about 0.1 and 2 percent in the ophthalmic medium. At 1 percent solution of 2-OH saclofen in water would be a likely concentration for clinical use. Alternatively, a 1 percent solution of phaclofen, 5-aminovaleric acid, 3-aminopropyl (diethoxymethyl) phosphinic acid, 3-aminopropyl (n-hexyl) phosphinic acid, and 3-aminopropyl phosophonic acid may be used clinically. Some constraints in formulation may exist having to do with pH and preservative. A pH of about 6.5 is expected to be acceptable as an ophthalmic drop and practical in terms of known solubility and stability of $GABA_B$ antagonists. Phosphate buffering is also common for eye drops and may be necessary with GABA$_B$ antagonists. Other additives and ingredients may be present, e.g., those disclosed in Chiou, U.S. Pat. No. 4,865,599, at column 3, lines 7 to 50, which disclosure is incorporated herein by reference. Common regimens for application of eye drops vary from one time a day to four times a day spaced evenly throughout waking hours. More effective agents may require fewer applications or enable the use of more dilute solutions. Alternatively, ointments, solid inserts and local depositors of powders are now coming into increased use in clinical practice. They avoid problems of drug decomposition while delivering a defined amount of drug. It is, of course, also possible to administer the above-described active agents in therapeutically effective amounts and dosages in pills, capsules, or other preparations for systemic administration.

In experiments in animals such as those mentioned hereinabove in which axial myopia has been experimentally induced by depriving the retina of formed images, it has been noted by others in primates that amblyopia was also experimentally and coincidentally induced. Amblyopia is evidenced by poor visual acuity in the eye resulting in poor visual performance. Normally, visual acuity improves during maturation. It is known that axial amblyopia may occur in humans from unknown causes or as part of strabismus. It is likely that administration of therapeutically effective amounts and dosages of the gamma aminobutyric acid antagonist, e.g., 2-OH saclofen, might prevent or inhibit the development of permanent or persistent amblyopia in maturing humans. It is also likely that humans who have already developed amblyopia from other or even unknown causes might be aided by similar therapeutic treatment with the aforementioned agents.

Various modifications of the invention in addition to those shown and described herein will be apparent to those skilled in the art from the foregoing description. Such modifications are also intended to fall within the scope of the appended claims.

What is claimed is:

1. A method of controlling the abnormal postnatal growth of the eye of a maturing animal which comprises the ocular administration of a therapeutically effective amount of a GABA$_B$ receptor antagonist.

2. A method of inhibiting the abnormal postnatal axial growth of the eye of a maturing animal during conditions ordinarily leading to said abnormal growth, which comprises administering to said eye during postnatal maturation a therapeutically effective amount of a GABA$_B$ receptor antagonist.

3. The method of claim 2 wherein the antagonist is selected from the group consisting of 2-OH saclofen, phaclofen, 5-aminovaleric acid, 3-aminopropyl (diethoxymethyl) phosphinic acid, 3-aminopropyl (n-hexyl) phosphinic acid, and 3-aminopropyl phosophonic acid.

4. A method of inhibiting the abnormal postnatal axial growth of the eye of a maturing animal during conditions ordinarily leading to said abnormal growth, which comprises administering to said eye during postnatal maturation a therapeutically effective amount of 2-OH saclofen in a carrier or diluent buffered to a pH suitable for ocular administration.

* * * * *